(12) United States Patent
Fenton et al.

(10) Patent No.: US 10,682,509 B2
(45) Date of Patent: Jun. 16, 2020

(54) MULTIPLE NEGATIVE ELECTRODES

(71) Applicant: Sky Medical Technology Ltd, Cheshire (GB)

(72) Inventors: Jonathan Fenton, Greenwich (GB); Duncan Bain, Kings Langley (GB); Martin Gordon, Buckinghamshire (GB); Benjamin Gordon, Cambridge (GB)

(73) Assignee: Sky Medical Technology Ltd, Cheshire (GB)

( * ) Notice: Subject to any disclaimer, the term of this patent is extended or adjusted under 35 U.S.C. 154(b) by 166 days.

(21) Appl. No.: 15/739,272

(22) PCT Filed: Jun. 24, 2016

(86) PCT No.: PCT/GB2016/051902
§ 371 (c)(1),
(2) Date: Dec. 22, 2017

(87) PCT Pub. No.: WO2016/207655
PCT Pub. Date: Dec. 29, 2016

(65) Prior Publication Data
US 2018/0185630 A1    Jul. 5, 2018

(30) Foreign Application Priority Data

Jun. 25, 2015  (GB) .................................. 1511205.5

(51) Int. Cl.
*A61N 1/04* (2006.01)
*A61N 1/36* (2006.01)

(52) U.S. Cl.
CPC ......... *A61N 1/0452* (2013.01); *A61N 1/0456* (2013.01); *A61N 1/0476* (2013.01);
(Continued)

(58) Field of Classification Search
CPC ...... A61N 1/04; A61N 1/0404; A61N 1/0408; A61N 1/0424; A61N 1/044; A61N 1/0456;
(Continued)

(56) References Cited

U.S. PATENT DOCUMENTS

| 2003/0093133 A1* | 5/2003 | Crowe | ............... A61N 1/36003 607/72 |
| 2003/0187490 A1* | 10/2003 | Gliner | ................. A61N 1/0531 607/116 |

(Continued)

FOREIGN PATENT DOCUMENTS

| KR | 20140075905 A | 6/2014 |
| WO | WO 98/56455 A1 | 12/1998 |

(Continued)

OTHER PUBLICATIONS

International Search Report and Written Opinion dated Oct. 13, 2016 in connection with International Application No. PCT/GB2016/051902.
(Continued)

*Primary Examiner* — Eugene T Wu
(74) *Attorney, Agent, or Firm* — Wolf, Greenfield & Sacks, P.C.

(57) ABSTRACT

The present invention relates to a device for providing neuromuscular stimulation. The device comprises a positive electrode, a plurality of negative electrodes, a non-conductive substrate and a control unit for activating the electrodes. The control unit of the device activates the negative electrodes in a predetermined sequence, so as to deliver electrical stimulus to a user, wherein the predetermined sequence is repeated with an increasing level of stimulus until a predetermined outcome is achieved. Additionally each negative electrode of the devices comprises at least one conductive track mounted on the non-conductive substrate (Continued)

wherein at least one pair of negative electrodes overlap such that the conductive track or tracks of a first negative electrode of the pair overlap with the electrode footprint, but not the conductive tracks, of a second negative electrode of the pair.

21 Claims, 18 Drawing Sheets

(52) U.S. Cl.
CPC ....... *A61N 1/0492* (2013.01); *A61N 1/36003* (2013.01); *A61N 1/36007* (2013.01); *A61N 1/36034* (2017.08); *A61N 1/046* (2013.01)

(58) Field of Classification Search
CPC .. A61N 1/0472; A61N 1/0476; A61N 1/0492; A61N 1/0553; A61N 1/0597; A61N 1/36014; A61B 2562/04; A61B 2562/043; A61B 2562/046
See application file for complete search history.

(56) References Cited

U.S. PATENT DOCUMENTS

| | | | |
|---|---|---|---|
| 2004/0158298 A1* | 8/2004 | Gliner | A61N 1/0531 607/48 |
| 2010/0030298 A1* | 2/2010 | Martens | A61N 1/0529 607/45 |
| 2010/0076521 A1 | 3/2010 | Choi et al. | |
| 2012/0041513 A1* | 2/2012 | Tucker | A61N 1/36003 607/48 |
| 2013/0282091 A1* | 10/2013 | Leven | A61N 1/0553 607/116 |
| 2014/0324122 A1 | 10/2014 | Zierhofer | |
| 2016/0361533 A1* | 12/2016 | Savage | A61N 1/046 |

FOREIGN PATENT DOCUMENTS

| | | |
|---|---|---|
| WO | WO 03/006106 A2 | 1/2003 |
| WO | WO 2005/075018 A1 | 8/2005 |
| WO | WO 2006/054118 A1 | 5/2006 |
| WO | WO 2007/015907 A2 | 2/2007 |
| WO | WO 2010/066817 A2 | 6/2010 |
| WO | WO 2010/070332 A1 | 6/2010 |
| WO | WO 2014/001778 A1 | 1/2014 |

OTHER PUBLICATIONS

International Preliminary Report on Patentability dated Jan. 4, 2018 in connection with International Application No. PCT/GB2016/051902.

Great Britain Search Report dated Jan. 18, 2016 in connection with Great Britain Application No. 1511205.5.

Heller et al., Automated setup of functional electrical stimulation for drop foot using a novel 64 channel prototype stimulator and electrode array: Results from a gait-lab based study. Medical Engineering & Physics. 2013; 35:74-81.

* cited by examiner

A

B electrical field overlap of electrical fields electrode footprint conductive track electrical field electrode footprint conductive track

A

B side view b first layer – top view c

A

B

MULTIPLE NEGATIVE ELECTRODES

RELATED APPLICATIONS

This application is a national stage application under U.S.C. § 371 of PCT International Application No. PCT/GB2016/051902, filed Jun. 24, 2016, which claims foreign priority benefits under 35 U.S.C. § 119(a)-(d) or 35 U.S.C. § 365(b) of British application number 1511205.5, filed Jun. 25, 2015, the contents of each of which are incorporated herein by reference in their entireties.

FIELD OF THE INVENTION

The present invention relates to a device and method for neurostimulation.

BACKGROUND TO THE INVENTION

A method and device for providing electrical stimulation to a patient has previously been described in our international patent applications WO 2006/054118, WO 2010/070332 and WO 2014/001778. The contents of these publications are incorporated herein by reference.

When directly stimulating a nerve with superficial electrodes, it is well established in conventional Functional Electrical Stimulation that the current required to provide effective stimulation depends on the positioning of the electrodes relative to the nerve. The closer that the direct current path between electrodes passes to the nerve motor point in question, the less current is required to stimulate the nerve. Similarly, a given current is more effective in eliciting a muscle contraction if it passes closer to the specific motor nerve point. Therefore, the effectiveness of a nerve stimulation device comprising a simple pair of electrodes is highly dependent on the correct positioning of the electrodes. Consequently, in neuromuscular stimulation devices, it is necessary to apply an electrode to a suitable place on the body to stimulate a nerve. Frequently this position is not optimal in the first instance, and repeated attempts are required to position the electrode in the best position. This also applies to other types of stimulation, and to other applications for electrodes, including recording modes such as electromyography (EMG).

The optimal position for an effective electrode for stimulation of a particular nerve can be determined by sequential activation of subsets of electrodes chosen from an array. This allows the site of stimulation to be moved electronically rather than physically in relation to the nerve. The subsets of activated electrodes form distinct "virtual electrodes" or effective electrodes. Within such an electrode array, each electrode may be paired with its counterpart in an adjacent row in sequence. The direct current path between the activated electrodes, and hence the effective electrode, can thereby be moved incrementally as different pairs of electrodes are addressed. This allows for sequential adjustment of the position of the effective electrode, enabling the device to scan across a region, allowing the current path to pass very close to the optimum stimulation point, wherein the optimum pair of electrodes is addressed. This makes the positioning of the device relative to the nerve, for example on the skin, much less critical.

Heller et al. Medical Engineering & Physics 35 (2013), pages 74-81, describes a method for electrical stimulation of the leg in order to correct foot drop. Stimulation is delivered via a 4×4 subset of electrodes, chosen automatically according to a computer algorithm from an 8×8 array.

The applicant's previous patent application WO 2006/054118 describes an array of electrodes on a single substrate, allowing adjustment and selection of different positions of the effective electrode without removal or repositioning of the assembly.

International patent application WO 2007/015907 relates to a device comprising an electrode array for implanting into the tissue, in particular cardiac tissue. Different electrode subsets from the array can be activated in order to produce localised electrical fields.

US patent application US 2010/0076521 relates to a device comprising an electrical stimulation system for generating virtual channels for transferring external signals to nerve fibres and then the brain, for example for the purpose of restoring patients' vision or hearing. The virtual channels result from the overlap of the electrical fields of the individual electrodes within an electrical array, and thereby improve the resolution of neural stimulation.

The limitation of the array approach described in the above referenced publications is that, for a given electrode size, adjustments to the effective electrode position may only be made in whole units of the electrode, for example if the electrode is 1 cm×1 cm, the effective electrode position can only be adjusted in minimum increments of 1 cm.

Korean Patent Application KR 20120143273 describes an artificial cochlea for stimulating the auditory nerve. The electrodes of the device are positioned on conductive tracks surrounded by insulating layers. The insulating layers vary in size around the electrodes and the conductive tracks between the electrodes, such that the area of the conductive track between the electrodes is narrower than the area of the conductive track around the electrode. The arrangement allows for flexible positioning of the effective electrodes and thereby the electrical stimulus. As with an electrode array, the ability to adjust the position of the electrode may only be made in whole units of the electrode size formed by the conductive tracks.

When searching for the correct stimulation position, it would be advantageous to adjust the position of the effective electrode of a stimulation device in steps smaller than the electrode size. The present invention relates to electrode geometries which allow this.

SUMMARY OF THE INVENTION

According to a first aspect of the invention, there is provided a device for neuromuscular stimulation, comprising:
  a) a positive electrode,
  b) a plurality of negative electrodes,
  c) a non-conductive substrate and
  d) a control unit for activating the electrodes,
  wherein the control unit activates the negative electrodes in a predetermined sequence, so as to deliver electrical stimulus to a user, wherein the predetermined sequence is repeated with an increasing level of stimulus until a predetermined outcome is achieved,
  wherein each negative electrode comprises at least one conductive track mounted on the non-conductive substrate, and
  wherein at least one pair of negative electrodes overlap such that the conductive track or tracks of a first negative electrode of the pair overlap with the electrode footprint, but not the conductive tracks, of a second negative electrode of the pair.

The electrode footprint of an electrode is defined as the rectangular area centred on the electrode which has the same height and width as the electrode. By way of illustration, an electrode formed of a single linear conductive track 3 mm in length and 0.5 mm in width, has an electrode footprint comprising a 3 mm×0.5 mm rectangle centred on the electrode. An electrode formed by a circular ring of conductive track has an electrode footprint comprising a square of a width equal to the diameter of the circle formed by the outer edge of the ring. An electrode formed of a "V"-shaped conductive track has a footprint comprising a rectangle of height equal to the height of the V, and width equal to the width of the V. The area covered by the electrical field of an electrode is greater than the area of the footprint.

The electrical field of stimulation of a negative electrode of the present invention does not exactly correspond to the locus of the conductive tracks. This is because the conductivity in the surface stimulated by the electrode, for example the adhesive gel coupling the electrode to the skin or the surface layers of tissue, enables the electrical charge to 'spread out' from where the conductive tracks stimulate the surface. Similarly, the conductivity of the tissue below the skin means this "spreading" effect continues inside the body. These effects diffuse the margins of the conductive tracks and creates an electrical field of stimulation around the negative electrode. This has the effect of filling the gaps between the conductive tracks with electrical charge. Therefore the electrical field of a negative electrode formed from a cross-hatch pattern of conductive tracks will be similar to an electrode formed from a solid rectangle of conductive medium, wherein both electrodes have the same electrode footprint.

At least one pair of negative electrodes of the device of the present invention overlap such that the conductive track or tracks of the first negative electrode of the pair overlap with the electrode footprint, but not the conductive tracks, of the second negative electrode of the pair. Therefore, when the device searches for the optimal effective negative electrode position, it can move the effective electrode position from the first negative electrode to the second negative electrode wherein the conductive track of the first electrode overlaps with the electrode footprint formed by the adjacent electrode. In order that the device can adjust the position of the effective electrode in a step smaller than the electrode footprint of the first negative electrode, the distance between the first negative electrode and the second negative electrode is smaller than the length or width of the electrode footprint of the first negative electrode along the same axis. The invention thereby provides a higher degree of accuracy for locating the optimal effective electrode position than previously described stimulation devices possessing the same number of electrodes. The device of the present invention is therefore capable of achieving a greater degree of precision in finding the optimal stimulation point than the devices described in the prior art.

The first negative electrode of the pair may overlap with 0.5-1%, 1-10%, 10-25%, 25-50% or more than 50% of the footprint of the second negative electrode of the pair. More than one pair of negative electrodes of the device may overlap in the same manner as the first pair. The degree of overlap between pairs of negative electrodes in the device may be different for different pairs of negative electrodes. A single negative electrode may form an overlapping pair with more than one other negative electrode.

The device of the present invention may comprise a matrix of interlocking negative electrodes. By "interlocking" it is not meant that conductive tracks of the electrodes overlap, but that the conductive tracks of the electrodes approach one another at points or regions. The negative electrodes may interlock by interleaving, interdigitating and/or tessellating. Such geometrical arrangements decrease the size of the minimum spatial increments that are achievable when the device scans through the various effective negative electrode positions by activating each negative electrode in turn and/or sub-groups of negative electrodes in turn. The interlocking arrangement of the electrodes allows effective overlap of the electrical fields of the negative electrodes, thereby allowing movement of the effective negative electrode position by a fraction of the electrode footprint of each of the electrodes.

The embodiments described herein are directed to specific electrode geometries and patterns of interlocking negative electrodes of the device, but these are not intended to limit the invention and other electrode geometries and patterns of interlocking negative electrodes may be used.

In some embodiments of the invention the negative electrodes may tessellate. These negative electrodes may be arranged in a 2 dimensional array. The array may be 3×3, 4×4 or 8×8.

In alternative embodiments, the negative electrodes may form a radial pattern. In a preferred embodiment the radial pattern may contain a central negative electrode that interlocks with one or more of the radial electrodes. The radial pattern may be composed of 2, 3, 4, 5, 6, 7, 8 or more than 8 segments. In further embodiments, the tracks may form one or more radial borders around a central radial pattern. In further embodiments, the negative electrodes that form the radial border or borders may interlock with the negative electrodes that form the central radial pattern or the other radial border or borders.

In some embodiments, the first negative electrode of the overlapping pair may comprise at least 2 unconnected parallel tracks. The parallel tracks of the first negative electrode of the overlapping pair may be linear, zigzagged, curved, form a right-angle, form an acute angle and/or form an obtuse angle. In some embodiments, the device may comprise more than one such electrode wherein the parallel tracks formed by the electrodes interleave and are parallel with each other. In further embodiments, the device may comprise 2 or more such electrodes, wherein the parallel tracks are arranged such that the negative electrodes form a 2 dimensional array.

In some embodiments, the first negative electrode of the overlapping pair may comprise a central section of track from which issues a series of digits. In some embodiments these digits may be equally or unequally spaced. The digits may issue from either or both sides of the central section of track and/or be parallel to each other. The central section may be linear. The digits may be linear and/or perpendicular to the central section of track. Alternatively the digits may be curved. In further embodiments, the device may comprise 2 or more such electrodes, wherein the negative electrodes form a 2 dimensional array. In alternative embodiments the device may comprise 2 or more such electrodes, wherein the parallel tracks are arranged such that the electrodes form a radial pattern.

In further embodiments the first negative electrode of the overlapping pair may be a single zigzagged track. The zigzag may be "w" in shape. In some embodiments the zigzag may be regular. The internal angles of the zigzag may be a right angle, acute and/or obtuse. In further embodiments the device may comprise 2 or more zigzag negative electrodes wherein the zigzags are arranged such that the negative electrodes form a 2 dimensional array. In an alternative embodiment, the device may comprise 2 or more zigzag negative electrodes wherein the zigzags are arranged such that the negative electrodes form a radial pattern.

The negative electrodes of the device may be arranged in a single layer, such that the electrodes are all substantially parallel along a first axis which is perpendicular to their electrode footprints. A circuit could be produced by printed circuit technique, photoetching, conductive printing, or by other means, such that the negative electrodes could be arranged in an interlocking pattern. By sequentially addressing specific electrodes by means of a demultiplexer or analog switch or other means, a 2-dimensional electrode position can be selected, providing a means of scanning to locate the optimum stimulation point. In one variation, the position of adjacent electrodes in the pairs is addressable. In another variation, one electrode remains in a fixed position, but is paired with a 2-dimensionally selectable electrode, to allow positional control of the current path.

A further development of the above may comprise sequential selection of two or more subsets of electrodes. In an alternative embodiment, pairs or subsets of electrodes could be sequentially selected from such arrays, for example subsets of 3 adjacent negative electrodes from a radial array of 8 negative electrodes.

In further embodiments of the invention the negative electrodes may be arranged in more than one layer, wherein the electrodes of each layer are all substantially parallel along a first axis which is perpendicular to their electrode footprints. In a further embodiment the geometrical arrangement of the negative electrodes in the first layer may complement the geometrical arrangement of the negative electrodes on one or more of the other layers. In a further embodiment the negative electrodes in two or more layers may interlock with the negative electrodes of one or more of the other layers.

The conductive tracks of the electrodes of the device may be directly printed onto the non-conductive substrate, by conventional printing means (for example pad or tampo printing).

The non-conductive substrate may be in the form of an elongate strip or tongue, with the electrodes spaced along the strip. Such an arrangement may require an additional conductive track to be placed from the power supply to the further electrode, passing close to the nearest negative electrode. The non-conductive substrate may be flexible. The conductive tracks of the electrodes may also be flexible. In some embodiments, the device may comprise an elongate substrate having the control unit mounted towards the middle of the substrate; a set of negative electrodes may be located to one side of the control unit, and the positive electrode to the other side. Alternatively, the control unit may be located towards one side of the substrate, and all electrodes located on the other side of the substrate from the control unit.

The device may comprise one or more insulative strips or regions arranged to separate the conductive tracks of the negative electrodes from the adjacent negative electrodes; insulative strips may also or instead be arranged along the edges of the conductive strips to prevent current leaking outside the area of the strip. Alternatively, or in addition, the non-conductive substrate may comprise a recessed groove within which the conductive tracks may be located; thereby serving to separate the additional conductive track from the nearest negative electrode.

The device may be adapted to apply transcutaneous stimulation. In alternative embodiment the device may be configured to be implantable in a patient, for example, implantable subcutaneously. This would be of benefit in chronic indications where long term use of the device is required.

The device may further comprise a conductive gel overlying the electrodes. The gel is preferably in a single piece overlying the negative electrodes and the positive electrode, for ease of manufacture as well as structural integrity. A single piece of gel may be used, based on the bulk resistivity of the material and geometry, so that leakage resistance is much greater than delivery resistance. Examples of gels which may be used include hydrogel or silicone.

The device may be assembled as follows. The non-conductive substrate may be produced as a generally flat elongate strip and a recess forming a compartment. The negative electrodes and additional conductive track are then printed onto the non-conductive substrate, and the power supply and control means placed into the recess. This serves to connect all the electrical connections. The recess may then be closed, for example, by sonic welding a cover to seal the power supply and control means into the recess. Finally a gel is placed over the electrodes.

The device may further comprise a locating mark to aid correct placement in use.

The device may include a press button for activating or deactivating the device. The control means may be configured to provide a plurality of activation modes (for example, with different stimulation characteristics); the press button may be used to cycle through these modes. The device may include a display means, such as a light or an LED, to indicate the selected activation mode.

The device of the present invention may also be adapted to prevent leakage of current from the activated negative electrode(s) to the inactive negative electrodes, for example by driving the inactive electrodes to a potential such that they do not supply or draw current. This may be achieved by connecting the negative electrodes to a positive electrode or by using a capacitor to automatically adjust the voltage such that no current flows.

The device of the present invention could be used for the application of a variety of treatments. These may include, but are not limited to, improving blood circulation in a lower limb of a patient in order to treat deep vein thrombosis (DVT) and/or superficial vein thrombosis (SVT), leg ulcers (arterial, venous, or diabetic), varicose veins, dysfunctions of systemic circulatory effects of peripheral vascular disease (such as Intermittent claudication), ischaemic heart disease (such as angina, myocardial infarction and heart failure), ischaemic organ disease (such as liver, kidney, intestine), cerebro-vascular disease, common and pulmonary hypertension and/or osteoporosis. In other embodiments of the invention the device could be used to treat incontinence, preferably whereby the electrical stimulation is insufficient to cause muscle contraction of the muscles innervated by the stimulated nerve.

As described in the applicant's previous application WO 2006/054118, a possibly undesirable effect of isolated contraction of the calf muscles is the plantar-flexion of the foot. In a seated individual (such as an airline passenger), this may cause the knee to rise, so making the process more obtrusive. Isometric contraction ensures that opposing muscles or groups of muscles are stimulated such that there is no or little movement of the limb as a result. The stimulus may be applied directly to posterior calf muscles; conveniently the soleus and/or gastrocnemius muscles. Indirect stimulation of the lower limb muscles may be achieved by electrical stimulation of the lateral popliteal nerve in the region of the popliteal fossa. Specifically at the inner margin of the biceps femoris muscle, behind the fibula at the inner side of the tendon of the biceps femoris. Additionally, indirect stimulation of the lower limb muscles may be further achieved by electrical stimulation of the medial popliteal nerve, which is located medially from the lateral popliteal nerve in the region of the popliteal fossa.

A second stimulus may be applied to shin muscles; conveniently the tibialis anterior. Preferably the second stimulus is applied simultaneously to the stimulus applied to the calf muscles. While this may not promote blood flow, application of a stimulus only to a posterior calf muscle may have the unwanted side effect of causing movement of the ankle joint. Application of a stimulus to the shin muscle will counteract any movement of the ankle joint caused by contraction of the calf muscle, so keeping the ankle and knee joints relatively still.

Alternatively, stimulation of the lateral popliteal nerve, in the region of the popliteal fossa, has the advantage of initiating the contraction of both posterior and anterior lower limb muscle groups. Such simultaneous stimulation results in isometric contraction; hence the ankle and knee joints would not be typically mobilised. Stimulation of the lateral popliteal also elicits contraction of the foot muscles and hence the so-called "Foot-pump" thereby further stimulating emptying of venous blood and enhancing blood flow. Additionally, the surprising advantage of selective stimulation of the lateral popliteal nerve is that the resultant muscular contractions are entirely compatible with standing and walking. An additional benefit of this mode of indirect stimulation is the involvement of the muscles in the sole of the foot, which have been shown to contribute substantially to clearance of blood from the lower leg.

In a clinical environment, where standing and walking are not a pre-requisite, the medial popliteal nerve may be stimulated, either in isolation or in combination with stimulation of the lateral popliteal nerve. A preferred version of dual medial and lateral popliteal nerve stimulation may result in near maximal contraction of the entire lower limb musculature, leading to enhanced efficiency and activity of both the calf and foot venous pumps, and by extension, movement of venous blood out of the lower limb, centrally towards the abdomen.

Therefore, in a preferred embodiment the device of the present invention may be used in a method for inducing isometric muscle contraction, preferably wherein electrical stimulation is applied to a single nerve.

The device of the present invention may be used in a method for promoting circulation in a patient having a heart condition, the method comprising administering one or more electrical stimuli to a plurality of leg muscles sufficient to cause isometric contraction of the muscles. Electrical stimulation of the musculovenous pump promotes altered blood flow patterns, which may be beneficial in patients having heart conditions. The heart condition may include cardiac arrest, suspected cardiac arrest, arrhythmia, brachycardia, or angina. The method may also be used as an adjunct to defibrillation in the case of cardiac arrest. Also provided is a device for use in promoting circulation in a patient having a heart condition, the device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically. The invention also provides a kit comprising such a device in combination with a defibrillator. Alternatively, the device may include a defibrillator.

The device of the may be used in a method relating to the modification of cortical blood flow in bone. As noted in WO 2006/054118, the method of isometric muscle stimulation has been shown to promote cortical blood flow. Furthermore, as demonstrated in the Applicants' patent application WO 2010/070332, bone oxygenation and bone perfusion are increased by use of the method. This allows more effective delivery of pharmaceutical agents to the bone, particularly those intended for treatment of bone disorders including osteoporosis. Thus, the device of the present invention may be used in a method for improving administration of medicaments for treatment of bone disorders, the method comprising administering said medicament to a patient, and administering one or more electrical stimuli to a plurality of leg muscles sufficient to cause isometric contraction of the muscles and enhance bone perfusion. The bone disorder may be osteoporosis.

Improved perfusion may also be useful for improving delivery of contrast agents (for example for medical imaging purposes) to tissues such as the bones, tendons, ligaments, etc. The device of the present invention may therefore be used for improving delivery of contrast agents, the method comprising administering said contrast agent to a patient, and administering one or more electrical stimuli to a plurality of leg muscles sufficient to cause isometric contraction of the muscles and enhance perfusion of said agent.

A still further aspect of the invention relates to cosmetic therapy. As demonstrated in WO 2010/070332, use of the method therein increases peripheral blood circulation, in particular circulation in the skin. The method also increases skin temperature where circulation is increased. These effects may be of benefit in the cosmetic treatment of individuals. For example, the effects may include reduction of cellulite or collagen deposits, improvement of skin tone, or improvement of skin condition. Thus, the device of the present invention may be used for cosmetic treatment of a patient, the method comprising administering an electrical stimulus to at least one leg muscle of a patient sufficient to cause the muscles to contract isometrically. The cosmetic treatment may be selected from reduction of cellulite or collagen deposits, improvement of skin tone, or improvement of skin condition.

In some embodiments the device may be used to stimulate the sciatic nerve, tibial or popliteal nerve.

Successful application of treatment and/or identification of the optimum electrode pair or subset by the device will be determined by the achievement of a predetermined outcome. This could be achieved by user feedback, for example by pressing a button when the predetermined outcome is achieved. Alternatively, the device may comprise a sensor for monitoring whether the predetermined outcome is achieved. The sensor may have the facility for measuring blood clearance by PPG or other means. Blood pressure and/or circulation may be monitored, for example by a photoplethysmograph comprising an LED and light sensor arranged such that the sensor detects light from the LED reflected from the user's leg. Alternatively, the device may comprise a sensor for detecting motion of the dorsal reflex of the users foot or for audio/acoustics monitoring of the muscle.

Having established the optimum electrode pair, it would then be possible to address specifically those electrodes during the periodic stimulation.

In some embodiments of the invention, if the predetermined outcome is achieved the control unit may maintain the activation of the same negative electrodes or combination of negative electrodes that are activated at that time, and at the same level of stimulation. In this way, optimal activation may be maintained.

The control means is preferably a processor device having a stored program for activating one of more of the negative electrodes.

The control means is preferably adapted to repeatedly activate one or more of the negative electrodes in a predetermined sequence. The control means may additionally be adapted to repeat the predetermined sequence whilst applying increasing levels of current each time.

The control means is additionally adapted to receive feedback from the user or a sensor regarding whether a predetermined outcome is achieved. If the control means receives feedback that the predetermined outcome is achieved, the control means can be adapted to maintain the activation of the same negative electrode or combination of negative electrodes activated when the predetermined outcome was reached, and maintain the level of stimulation by the said negative electrode or negative electrode(s) when the predetermined outcome was reached.

The control means is preferably adapted to activate one or more of the negative electrodes to deliver a current of between 0 to 100 mA, preferably 0 to 50 mA, more preferably 1 to 40 mA, and most preferably between 1 to 20 mA.

The control means may be adapted to activate one or more of the negative electrodes to deliver an AC waveform, although preferably the control means is adapted to activate the electrode to deliver a DC waveform, more preferably a pulsed DC waveform. The waveform or pulse may have a frequency of 0.01 to 100 Hz, preferably 0.1 to 80 Hz, and most preferably 0.1 to 5 Hz. In other embodiments, the frequency may be 20 to 80 Hz, more preferably 30 to 60 Hz, and most preferably 40 to 50 Hz. Alternatively, a stimulus with a frequency from 0.1 to 1 Hz, or from 0.33 to 1 Hz may be used. The precise desired frequency may depend on the purpose of the method, and the general physical condition, age, sex, and weight of the patient, among other factors.

The control means preferably activates one or more of the electrode to deliver a stimulus for a duration between 0 and 1000 ms, between 100 and 900 ms, between 250 and 750 ms, between 350 and 650 ms, or between 450 and 550 ms. In certain embodiments, the stimulus may be applied for up to 5000 ms, up to 4000 ms, up to 3000 ms, or up to 2000 ms. Other durations may be used; again this may depend on the details of the patient.

The control means is adapted to vary characteristics of the stimulus over time. For example, a single stimulus may increase in current over the duration of the stimulus. Preferably the increase is gradual up to a peak; the stimulus may then either be maintained at the peak; terminate at the peak; or decrease in a gradual manner.

The electrode(s) may be of a generally conventional type; for example, reusable type like some TENS applications or disposable electrodes of the type commonly used for ECG applications. The electrodes may be self-adhesive; repositionable; semi-adhesive; or may include a conductive gel for ensuring skin contact. Alternatively, the stimulation device may comprise a conductive gel, or may comprise an alternative conductive medium for interposing between the electrode and a user's skin. For example, the device may comprise a liner impregnated with a conductive gel or electrolyte for location between the electrode and a user. The liner may be conductive in restricted locations; for example, at a number of locations over the liner. This allows stimuli to be applied at a number of locations on a user's limb using only a single electrode.

The device may be adapted for stimulating the leg of a patient. The device may further comprise means for applying compression to the lower leg of a user. For example, the device may comprise a compression stocking or similar arrangement. The means for applying compression may also serve to carry one or more electrodes. For example, the electrodes may be mounted on a compression stocking, or on a band which fits around a user's leg, either in the calf area or on the knee area. Such a band may comprise neoprene or another similar elastic material. Alternatively, the electrodes may be mounted on an elastic material adapted to be wrapped around a user's leg; this allows the compression exerted by the material to be modified for different users.

In certain embodiments of the invention, the electrodes may be mounted on a band or wraparound material, which does not apply compression to the leg of a user. The use of a band or wraparound material allows placement of electrodes to be predetermined by their location on the band, such that a degree of variability in user's placing of the electrodes may be reduced.

The device may further comprise means for monitoring blood characteristics. In particular, blood pressure and/or circulation may be monitored. Conveniently, the monitoring means may comprise a photoplethysmograph; conveniently this may comprise an LED and light sensor arranged such that the sensor detects light from the LED reflected from the user's leg.

The device may further comprise means for recording the monitored characteristics for later reference. For example, the recording means may comprise data storage means associated with the control means; the data storage means may be in the form of a solid state memory or similar.

The control means may further be adapted to adjust the activation of the electrode in response to the monitored blood characteristic. For example, the degree of stimulation may be adjusted to a level sufficient to ensure blood circulation, but no greater. Alternatively, stimulation may be effected only at such times as the monitoring indicates that blood circulation has reduced below a certain level.

The device may further comprise means for visually indicating when the electrode is activated; for example, an LED or other indicator may be activated when the electrode is. This provides a visual confirmation to a user that the device is functioning.

In certain embodiments, the control means of the device may be detachable from other components of the device. In particular, the control means may be detachable from the electrodes; in preferred embodiments, the electrodes are mounted on a support, and the control means is detachable from this support. The control means may be incorporated into a separate module; this module may also include a power supply, and other components where present, such as a visual indicator and/or blood pressure monitoring means. The module may include electrical contacts, which are engageable with corresponding contacts to connect the control means to the electrodes. The corresponding contacts may be located in a cradle or other receiving means, which receives the module comprising the control means. The cradle may also comprise mechanical engagement means, such as a detent or similar, to engage the module with the cradle. Alternatively, a magnetic engagement means may be used.

In certain embodiments the device may be disposable; for example, after a single use. The device is intended to be sufficiently small and light—for example, less than 10 cm in length, and weighing less than 100 g, preferably less than 20 g—so as to be highly portable.

In use the device may be operated so as to engender little or no noticeable skin sensation or discomfort when activated to stimulate muscle contraction.

BRIEF DESCRIPTION OF THE DRAWINGS

The present invention will now be described by way of example only and with reference to the accompanying drawings, in which.

DETAILED DESCRIPTION OF THE INVENTION

Figure 1:
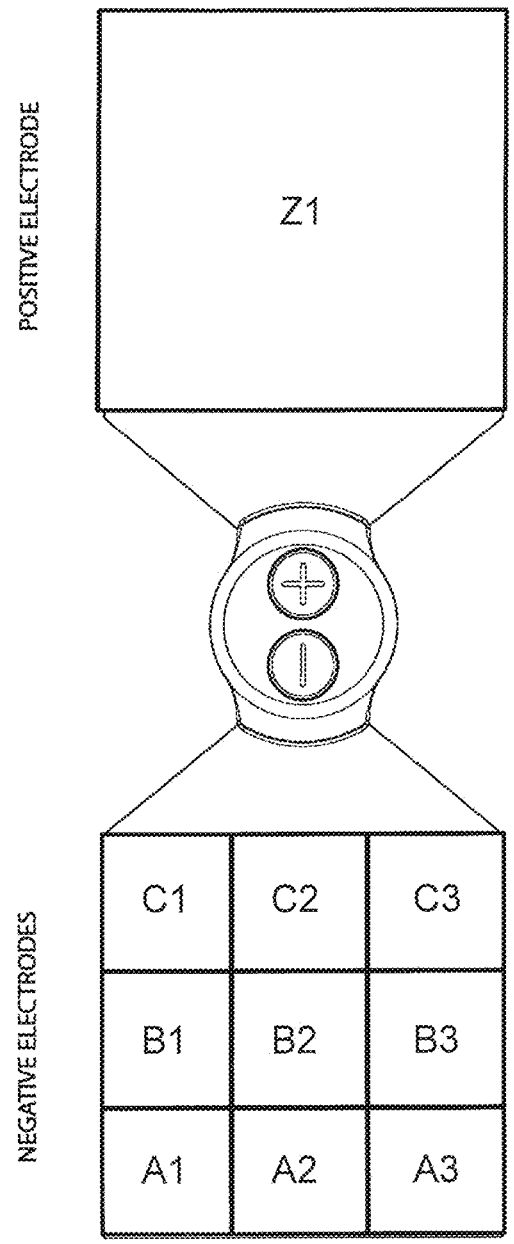
FIG. 1 is a schematic of an embodiment of a device for neuromuscular stimulation, comprising a 3×3 grid of negative electrodes and a positive electrode.

Referring first of all to FIG. 1, this shows a schematic of an embodiment of a device for neuromuscular stimulation. The device comprises a positive electrode (Z1) and a plurality of negative electrodes (A1-A3, B1-B3 and C1-C3) arranged in a 3×3 grid.

Figure 2:
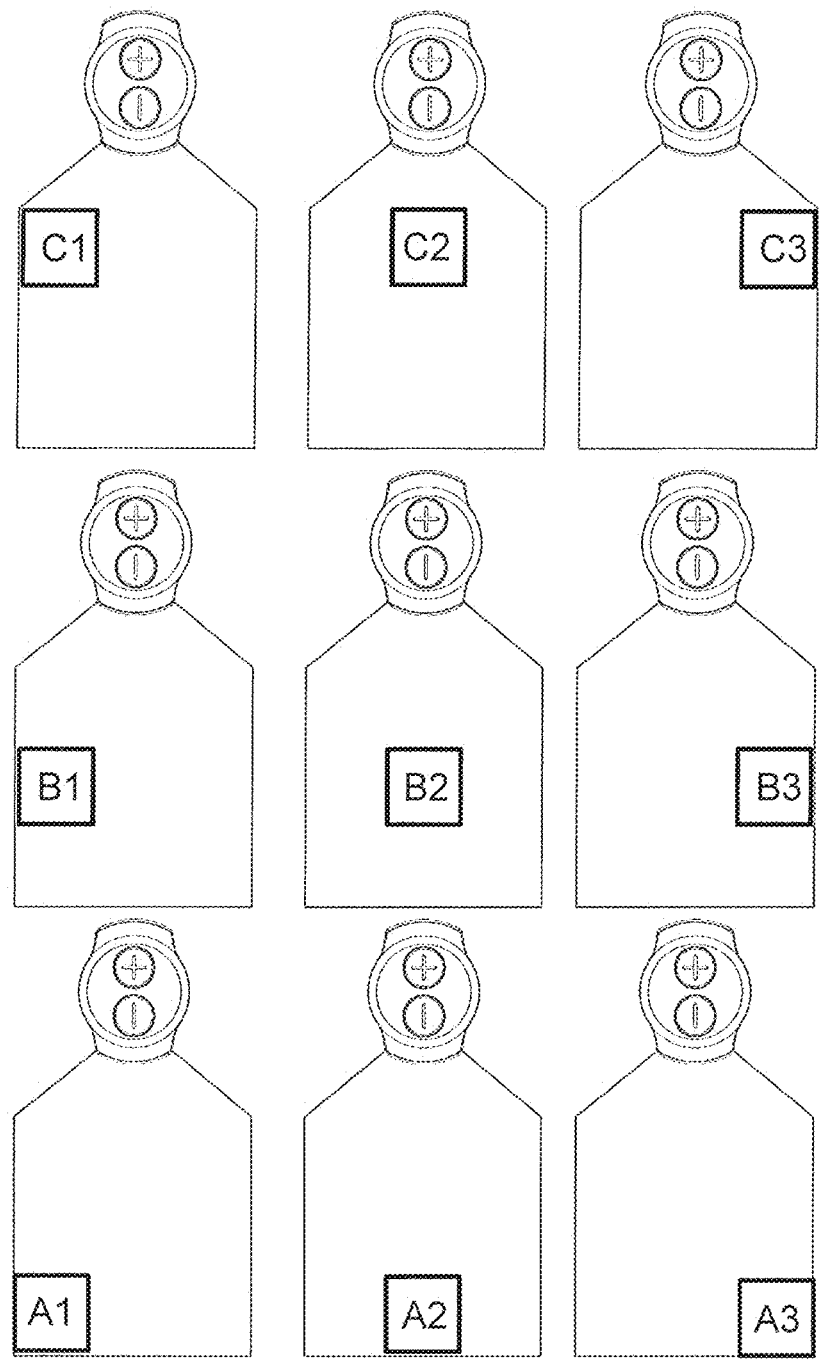
FIG. 2 is a schematic demonstrating the number of effective electrodes that could be individually activated within a 3×3 grid of electrodes.

FIG. 2 demonstrates the number of electrodes that can be individually activated within a 3×3 grid of electrodes, as well as the positions that they may occupy. Activation of these different electrodes from the 3×3 grid allows the position of the electrical stimulation to change, without a physical change in position of the device or its electrodes.

Figure 3:
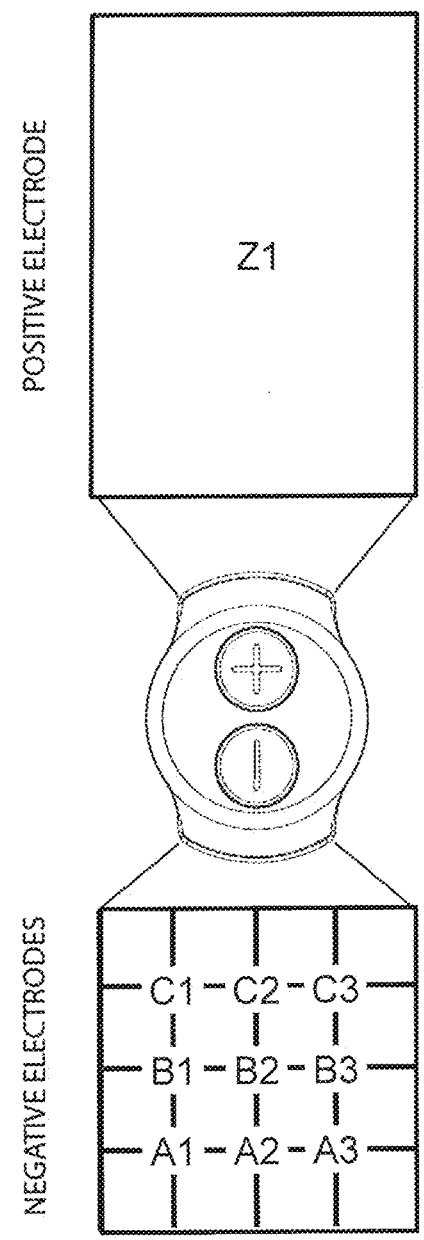
FIG. 3 is a schematic demonstrating a device for neuromuscular stimulation, comprising a grid of 3×3 virtual electrodes that could be activated by activating a subset of electrodes within a 4×4 grid of negative electrodes.

FIG. 3 demonstrates the concept of "virtual" or effective electrodes applied to a device for neuromuscular stimulation. The figure shows a schematic of a device for neuromuscular stimulation, comprising a grid of 4×4 physical electrodes and a positive electrode. Activation of these electrodes gives rise to the activation of a grid of 3×3 virtual electrodes (A1-A3, B1-B3, C1-C3). Each of the virtual electrodes can be individually activated by activation of a 2×2 subset of physical electrodes within the 4×4 array. The possibility of activating the virtual electrodes increases the number of effective electrode positions that the device can test in order to find the optimal effective electrode position. However, the limitation of this approach is that, for a given electrode size, adjustments to the effective electrode position may only be made in whole units of the electrode, for example if the electrode footprint is 1 cm×1 cm, the effective electrode position can only be adjusted in minimum increments of 1 cm.

Figure 4:
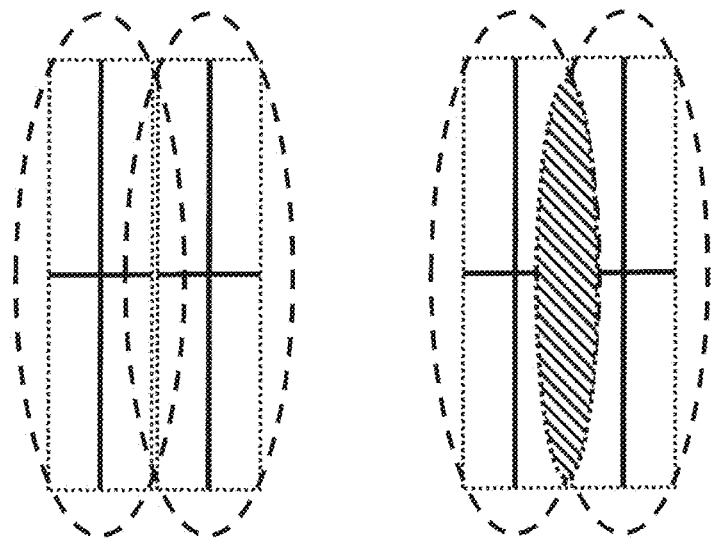
FIG. 4 is a schematic demonstrating the electrical fields and electrode footprints associated with electrodes formed of conductive tracks.
Figure 4:
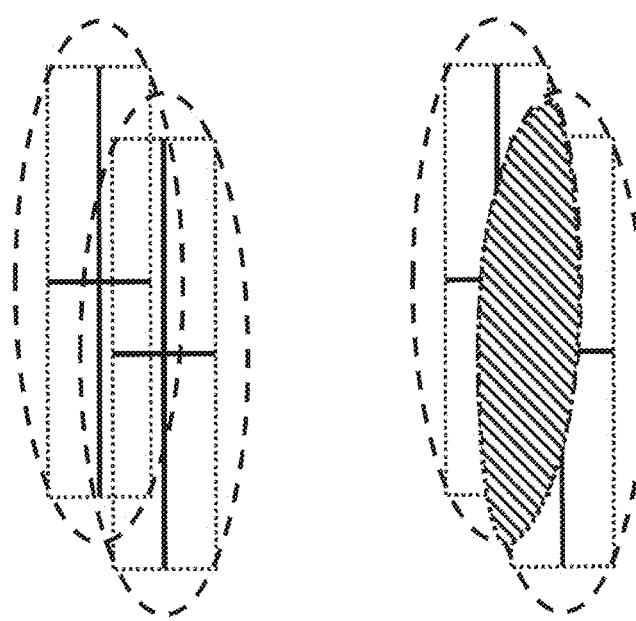
Figure 4:
Figure 4:
Figure 4:
Figure 4:

FIG. 4A is a schematic of 2 adjacent electrodes formed from 2 linear conductive tracks arranged in a cross shape. The non-overlapping electrode footprints of the electrodes are shown. The electrode footprint of an electrode is defined as the rectangular area centred on the electrode which has the same height and width as the electrode. The approximate electrical fields for both electrodes are also shown. The electrical fields overlap, producing a virtual electrode between the 2 physical electrodes. FIG. 4B is a schematic of 2 adjacent electrodes arranged according to one embodiment of the present invention. The conductive tracks of each electrode overlap with the electrode footprint of the other electrode. The conductive tracks of each electrode do not themselves overlap with each other. The degree of overlap of the electrical fields of these interlocking electrodes is greater than the degree of overlap of the electrical fields of the electrodes of FIG. 4A.

Figure 5:
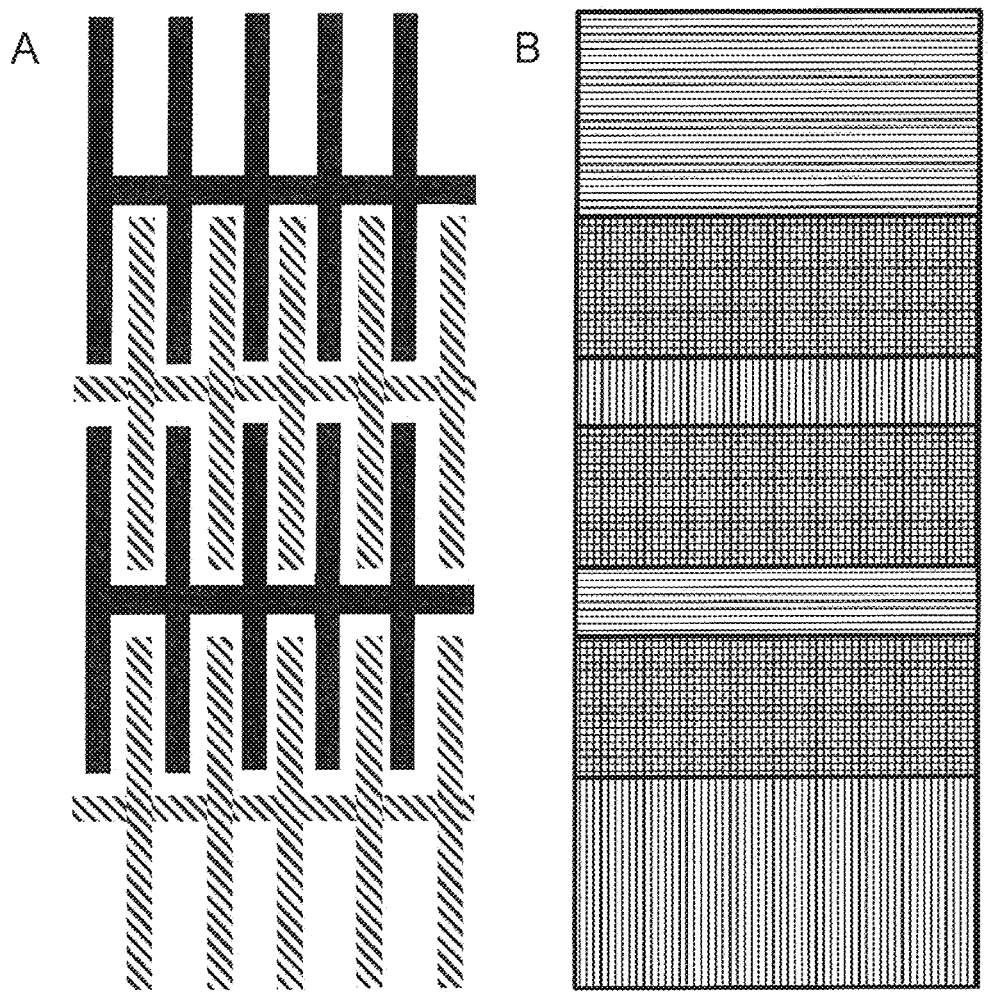
FIG. 5 is a schematic of interlocking electrodes formed of central sections of conductive track from which issue a series of linear and perpendicular digits, wherein the electrodes are arranged in a 1×4 matrix.

FIG. 5A is a schematic of 4 interdigitating electrodes that are formed of conductive tracks according to one embodiment of the invention. The conductive tracks of each electrode do not overlap with the conductive tracks of any other electrode. The electrodes are formed of conductive tracks comprising a central section of track from which issue a series of parallel and linear digits that are perpendicular to the central section of track. The interdigitating tracks allow effective overlap of each electrode with the electrode footprints of two adjacent electrodes, allowing movement of the effective electrode position formed by the virtual or effective electrode between pairs of interlocking electrodes by less than the width of the electrode footprint along the same axis. FIG. 5B is a schematic of the electrode footprints of the negative electrodes represented in FIG. 5A. The figure demonstrates that the conductive tracks of each negative electrode overlaps with the electrode footprint of at least one other negative electrode.

Figure 6:
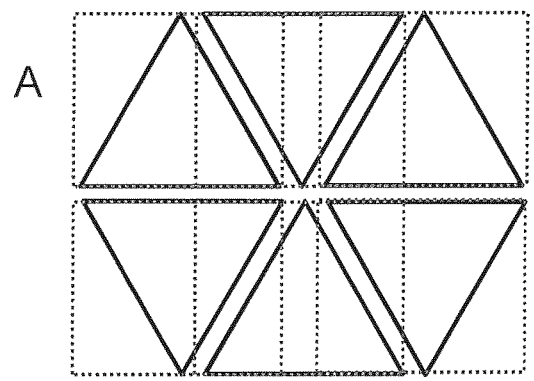
FIG. 6 is a schematic of interlocking triangular electrodes arranged in a radial pattern.
Figure 6:
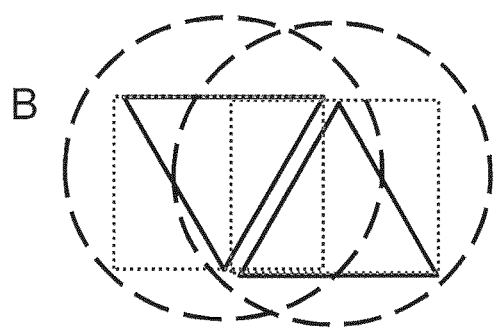
Figure 6:
Figure 6:
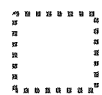
Figure 6:

FIG. 6A is a schematic of 6 electrodes formed of triangular conductive tracks, according to one embodiment of the invention. The electrodes form a tessellating pattern of triangles. The electrode footprints and conductive tracks of each of the electrodes are shown. The conductive track of each electrode overlaps with the electrode footprint, but not the conductive track, of an adjacent electrode. FIG. 6B is a schematic of the electrode footprints of two of the negative electrodes represented in FIG. 6A. The figure demonstrates that each negative electrode overlaps with the electrode footprint of at least one other negative electrode.

Figure 7:
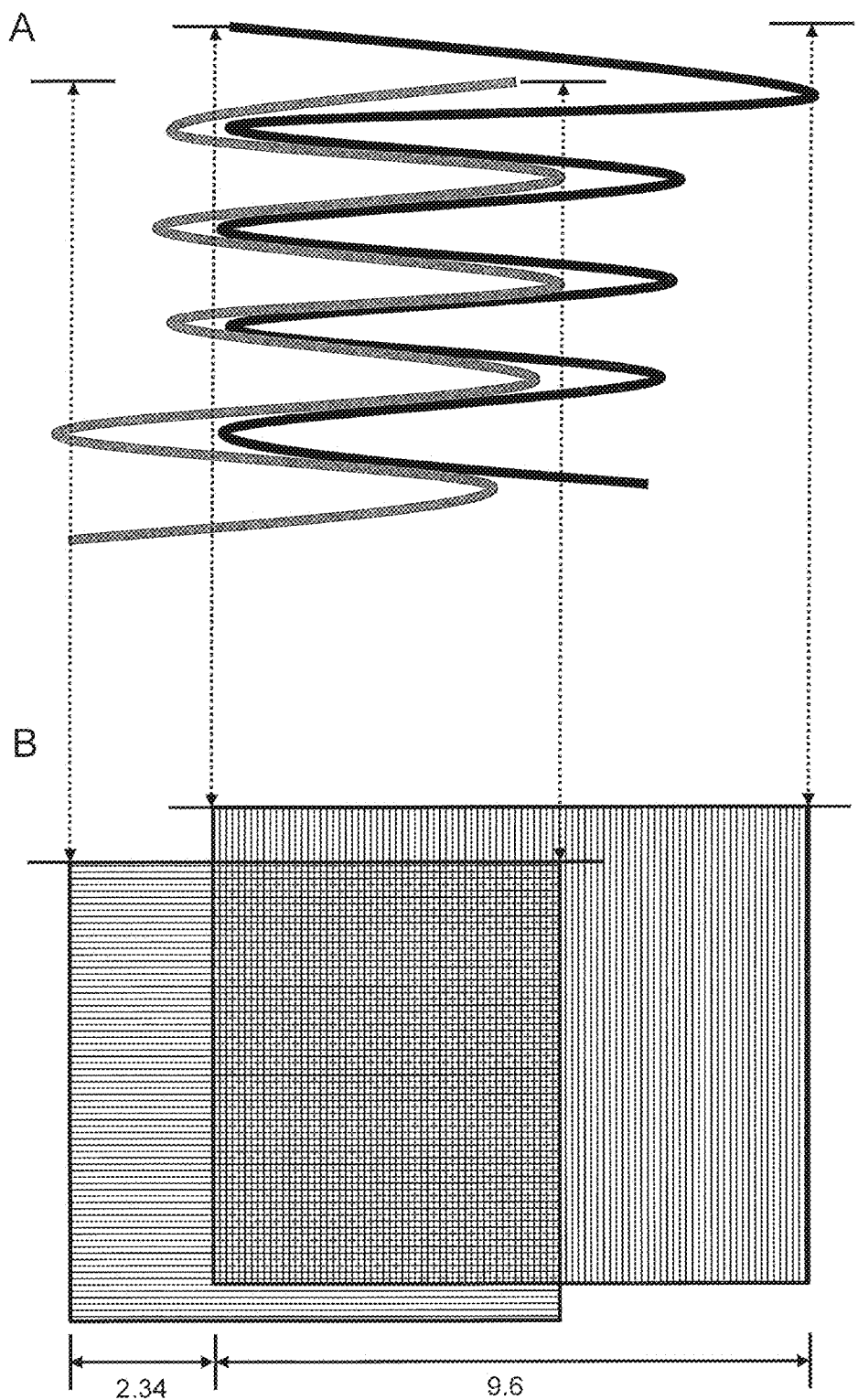
FIG. 7 is a schematic of interlocking zigzag electrodes arranged in a 1×2 matrix.

FIG. 7A is a schematic of 2 interlocking negative electrodes formed of conductive tracks that are zigzags, according to one embodiment of the invention. The electrodes are arranged in a 1×2 matrix. The conductive tracks of each electrode do not overlap with the conductive tracks of any other electrode. This arrangement of electrodes allows positional increments smaller than half the width or length of the electrode footprint along the same axis. FIG. 7B is a schematic of the electrode footprints of the negative electrodes represented in FIG. 7A. In this particular example, where each electrode is printed in W formation, positional increments by less than a quarter of the width of the electrode footprint are possible (e.g. 9.6/4=2.4>2.34). It will be appreciated that additional convolutions may be applied, and, within practical limits of track thickness, the spacing between the tracks may be reduced.

Figure 8:
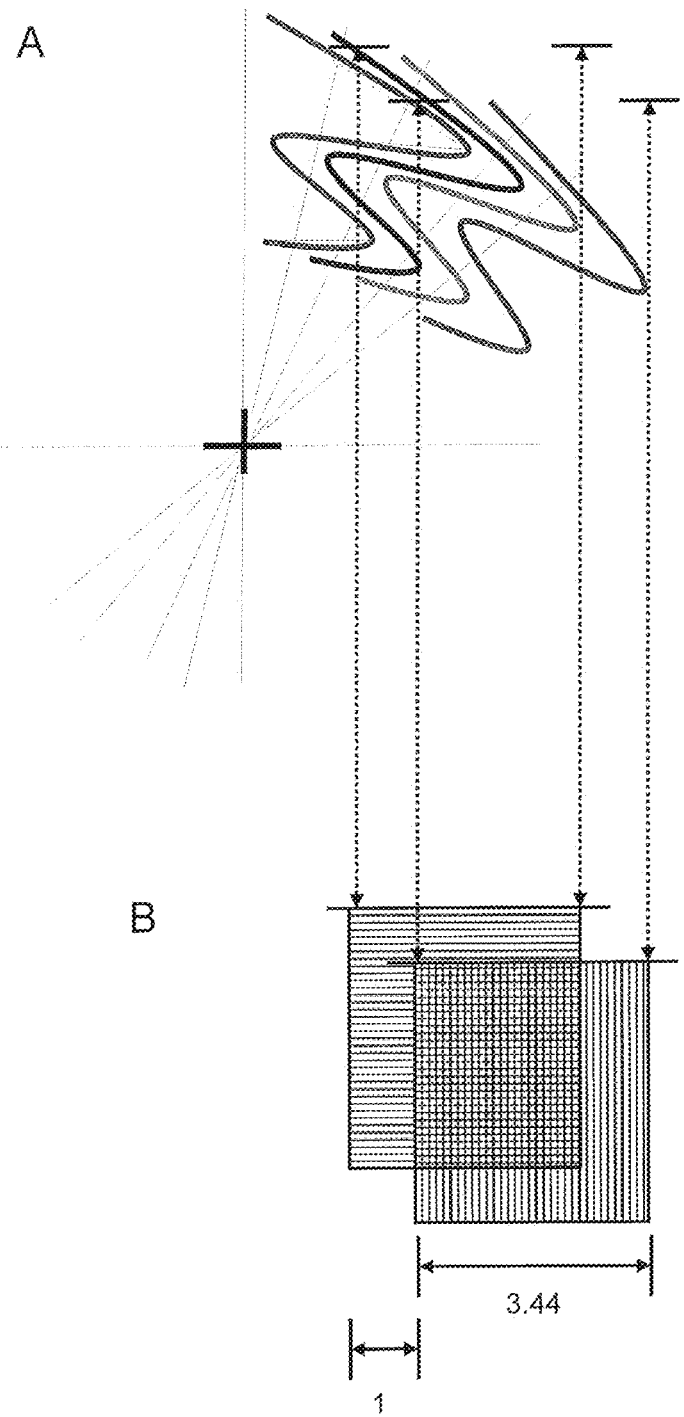
FIG. 8 is a schematic of interlocking zigzag electrodes arranged in a radial pattern.

FIG. 8A is a schematic of interlocking negative electrodes arranged in a radial pattern according to one embodiment of the invention, wherein the conductive tracks are formed of zigzags. The conductive tracks of each electrode do not overlap with the conductive tracks of any other electrode. FIG. 8B is a schematic of the electrode footprints of the negative electrodes represented in FIG. 8A. This arrangement allows angular increments around a circular segment array by positional increments of less than half of the electrode footprint of the electrodes along the same axis (3.44/2=1.7>1).

Figure 9:
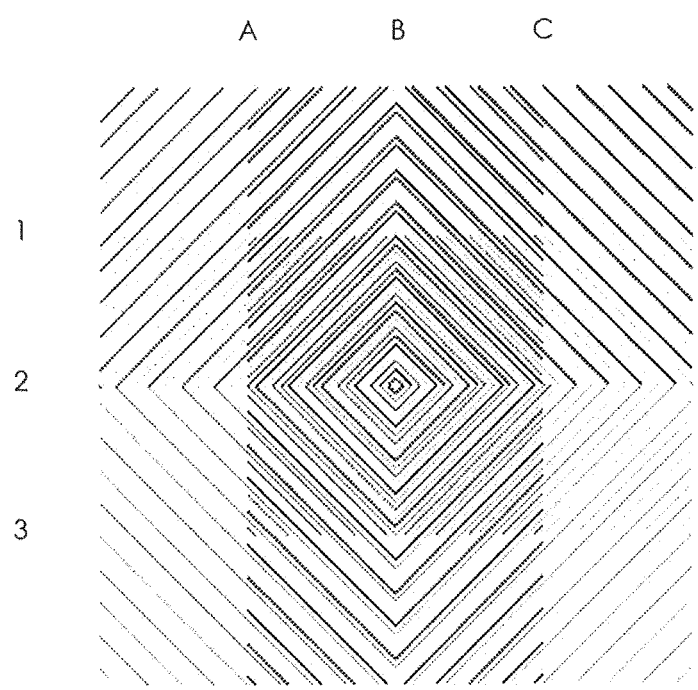
FIG. 9 is a schematic of the electrodes formed from parallel conductive tracks arranged in an interlocking 3×3 matrix.

FIG. 9 is a schematic of a 3×3 matrix of interlocking negative electrodes formed of a series of parallel conductive tracks. The conductive tracks of each electrode do not overlap with the conductive tracks of any other electrode. The parallel tracks of the electrodes are linear (A1, C1, A3, C3) or are a mixture of linear tracks and tracks that form a right angle (B1, A2, B2, C2, B3).

Figure 10:
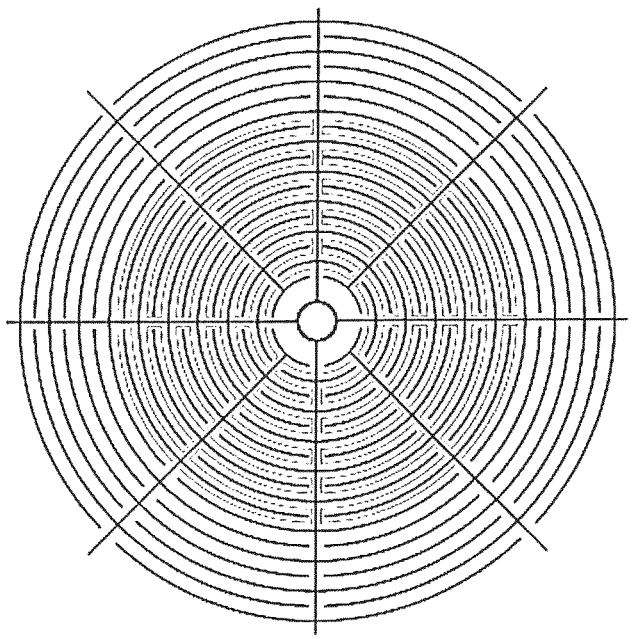
FIG. 10 is a schematic of interlocking electrodes arranged in a radial pattern, wherein the electrodes also interlock with a central electrode.
Figure 10:
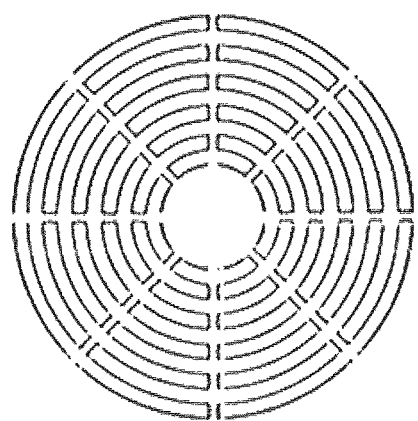
Figure 11:
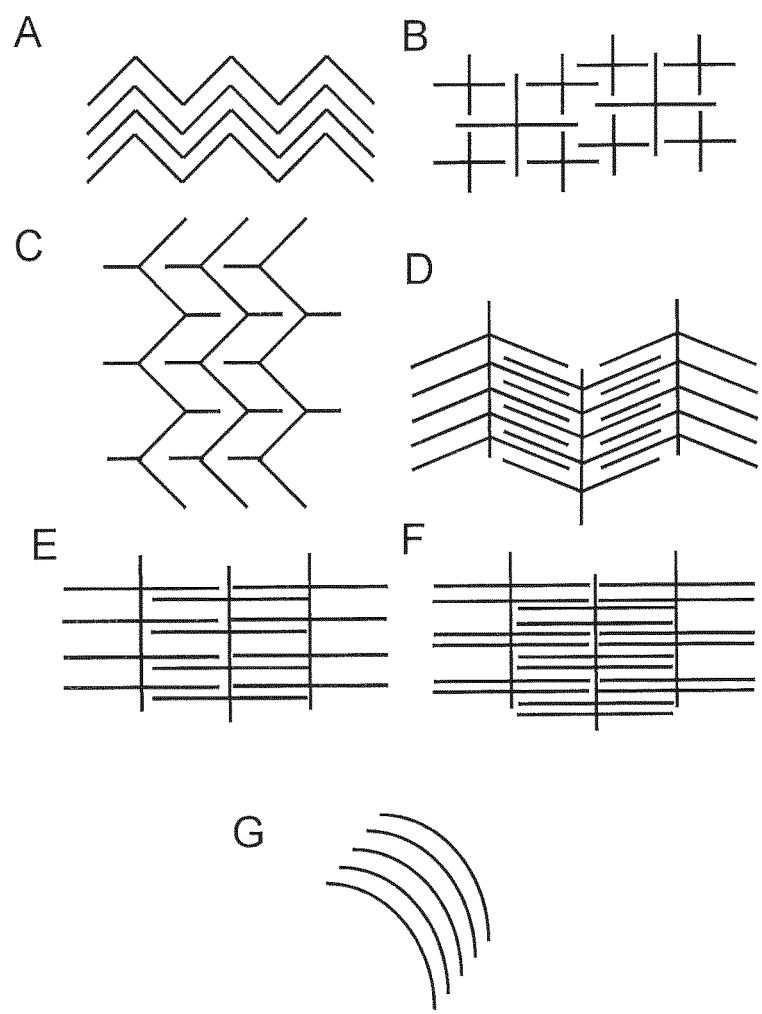
FIG. 11 is a schematic of a number of interlocking electrode geometries.

FIG. 10A is a schematic of a radial array of interlocking negative electrodes arranged around a central negative electrode. The radial electrodes interlock with the central electrode. The electrodes are formed of conductive tracks comprising a central section of track from which issue a series of parallel curved digits. FIG. 10B shows the shape of the central negative electrode in isolation.

FIGS. 11A-G shows a series of electrode geometries according to embodiments of the invention. It will be appreciated that many additional arrangements can be envisaged.

Figure 12:
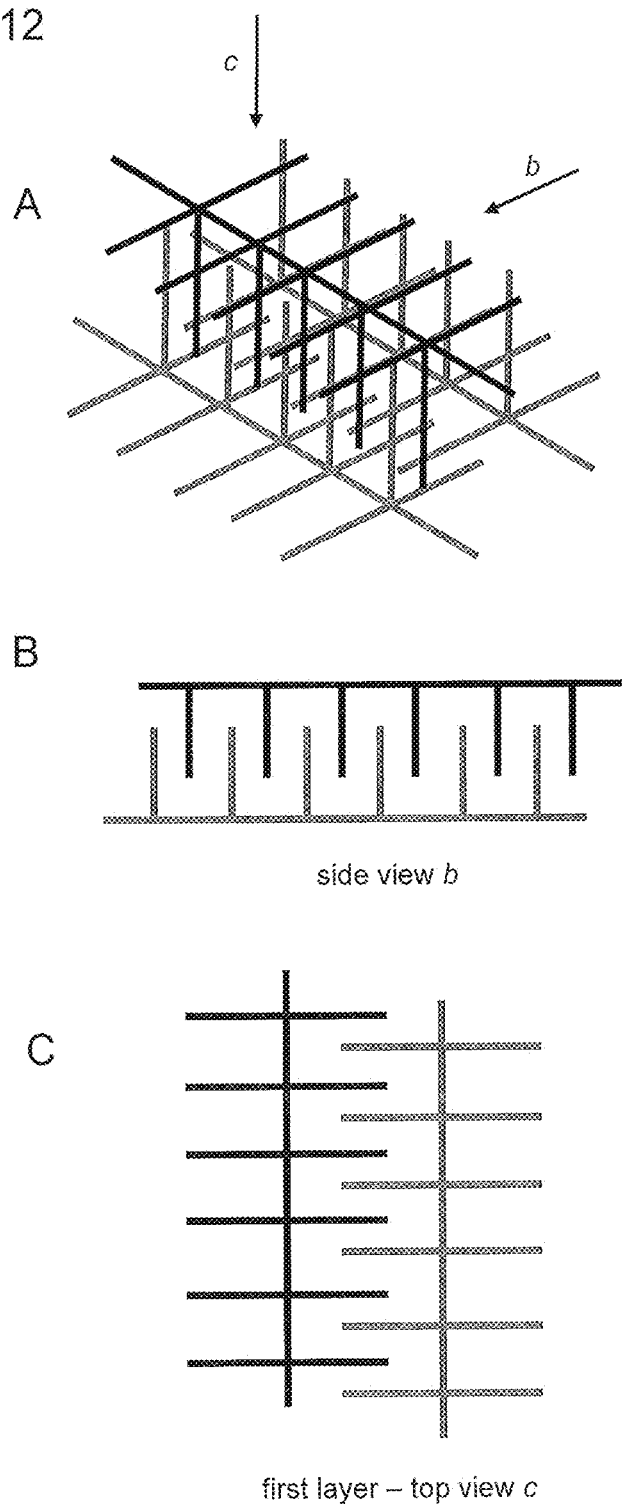
FIG. 12 is a schematic of interlocking electrode layers in 3 dimensions.

FIG. 12A is a schematic demonstrating interlocking layers of negative electrodes according to one embodiment of the invention. The first layer of electrodes are formed of conductive tracks comprising a central section of track from which issue a series of parallel and linear digits that are perpendicular to the central section of track in one axis (b), in addition to a series of parallel and linear digits that are perpendicular to the central section of track in another axis (c). The second layer of electrodes complement the first layer of electrodes such that the conductive tracks of each electrode interlock on both axes. The view along axes b and c are shown in FIGS. 12B and 12C respectively.

The negative electrode geometries described above for various embodiments of the invention decrease the minimum distance possible between adjacent negative electrodes of the device. When the device according to the present invention searches for the optimal effective negative electrode position, it can move the effective electrode position from one electrode or group of electrodes to a second electrode or group of electrodes, wherein the second electrode is within the electrode footprint of the first, and therefore closer than an adjacent, non-overlapping second electrode. The conductive tracks are an important feature of the invention. The fact that the electrodes are formed of conductive tracks enables effective overlap of an electrode with the electrode footprint of another electrode composed of a conductive track. This would not be possible, for example, with point electrodes within an electrode array. The invention thereby provides a higher degree of accuracy for locating the optimal effective electrode position than previously described stimulation devices possessing the same number of electrodes. The device of the present invention is therefore capable of achieving a greater degree of precision in finding the optimal stimulation point than the devices described in the prior art.

Figure 13:
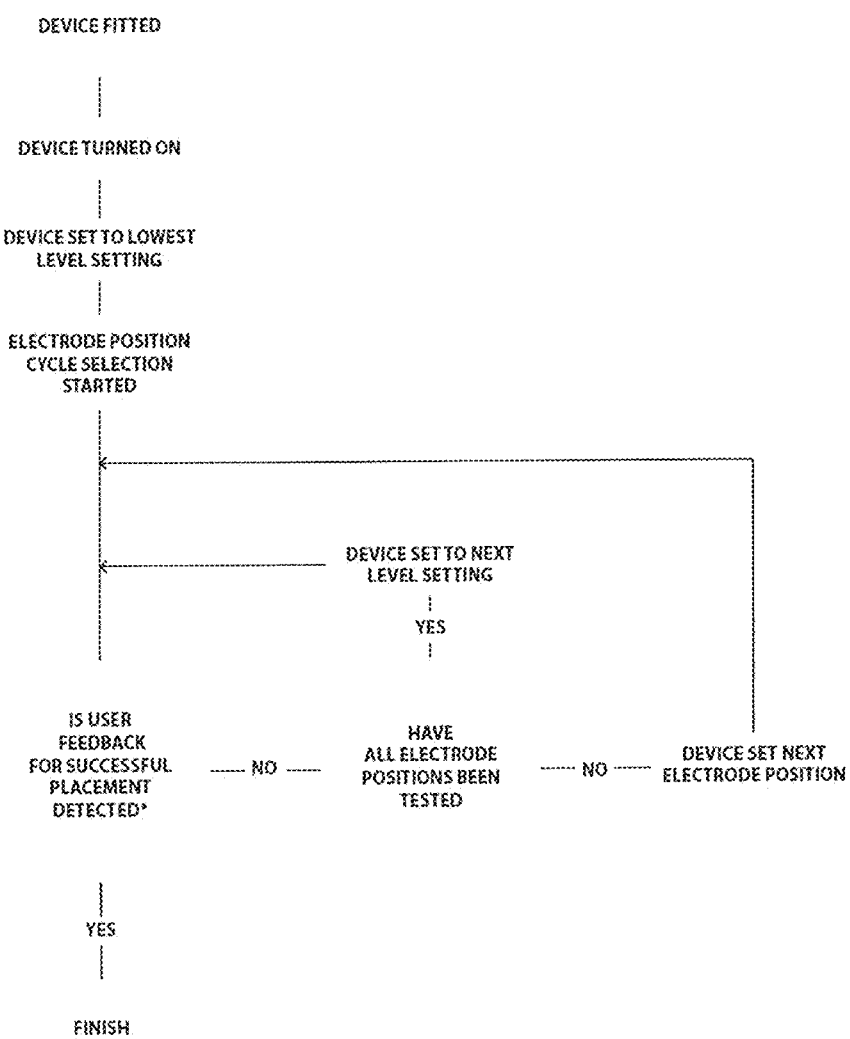
FIG. 13 is a flow chart describing the use of a device for neuromuscular stimulation where the position of the electrical stimulation is optimised.

FIG. 13 is a flow chart describing the use of a device for neuromuscular stimulation where the position of the electrical stimulation is optimised. The device is positioned on the skin and turned on. The device is first set to the lowest setting and activates in turn each negative electrode position. The user or automated systems within the device such as audio or acoustics monitoring of the muscle or blood flow or motion detection of the dorsal reflex of the users foot, provides the device with feedback that indicates for each electrode position whether the position induces the level of stimulation required to achieve a predetermined outcome, for example muscle contraction. If the device cycles through all the possible electrode positions without receiving feedback that the predetermined outcome has been achieved, the device is set to the next highest level setting. The device then cycles through all of the electrode positions once again until the predetermined outcome is achieved. This is continued through all the stimulation level settings until the predetermined outcome is achieved.

EXAMPLE 1

This example provides experimental validation for the use of a multi-electrode array comprising a pair of negative electrodes according to the invention, wherein the effective electrode position can be moved from the first electrode of a pair to a second electrode of the pair in steps smaller than the electrode footprint of the first electrode of the pair.

Materials and Methods

The Example uses two printed circuit boards (PCBs); a "stimulator" PCB and "sensor" PCB. The stimulator applies electrical stimulation to the sensor, and the sensor measures the position and magnitude of this stimulation.

Sensor PCB

The sensor comprises a grid of small pads and resistors designed to simulate the electrical conductivity of human skin and measure current flow. The pads of the sensor are grouped in columns. The electrical current in a column is fed into a current measuring shunt resistor. The voltage across the shunt resistor can be measured and the current density calculated using the known area of the column of pads connected to the shunt resistor.

Figure 14:
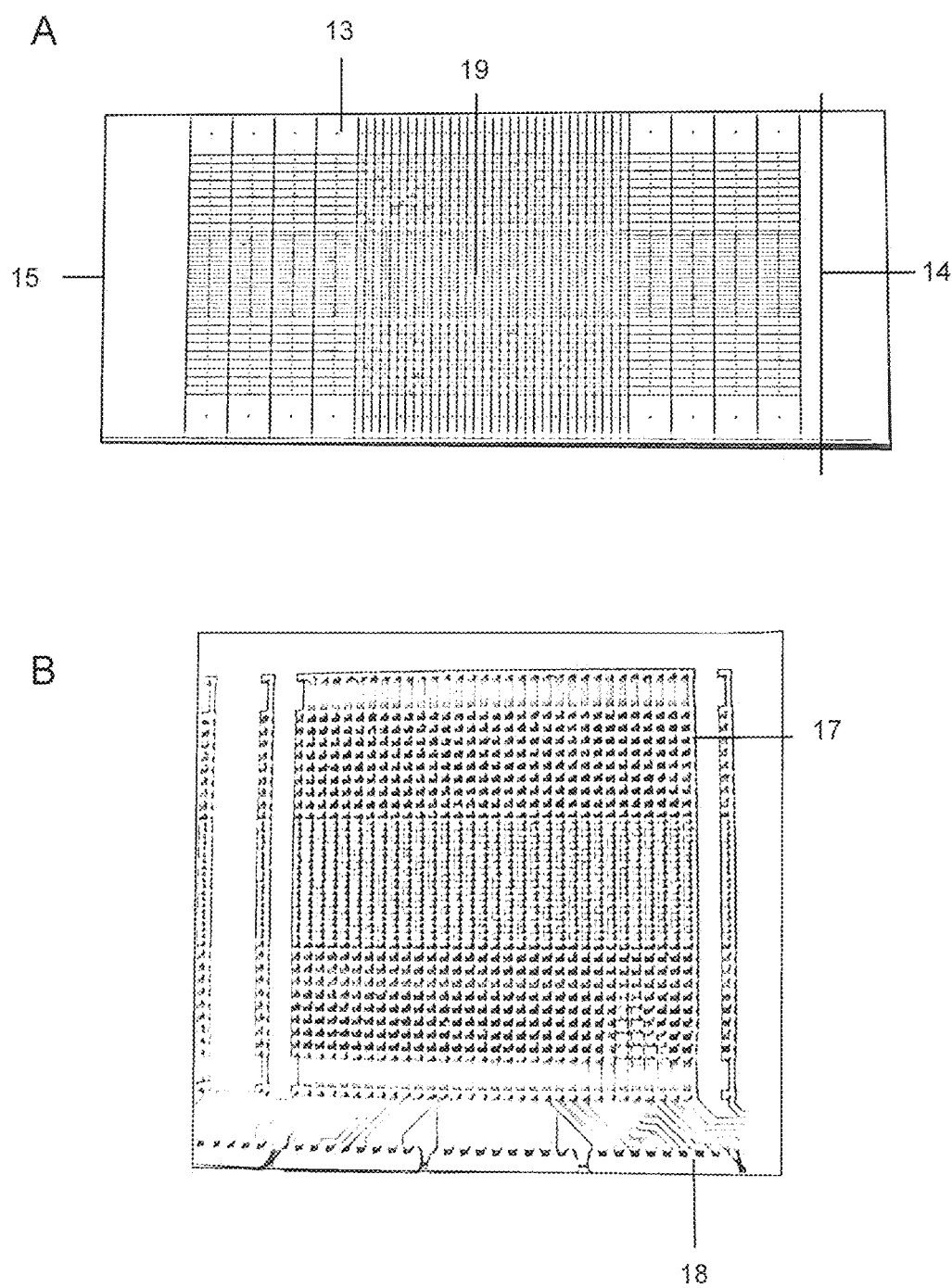
FIG. 14 is a photograph of the top and bottom of a sensor PCB.

FIG. 14 shows an example sensor PCB 15, comprising an array of pads 13 on one side (A) with resistors 17 and current shunt resistors 18 on the other side (B). Each column of pads 14 is connected together. The combined current is passed through a 10Ω 0 current measuring shunt 18. The pads 13 of the sensor increase in size as they approach the peripheral edges of the sensor 15, such that the centre section 19 of the sensor has the smallest pads 13 (1×2 mm). The centre section 19 is the area covered by the stimulator PCB. This arrangement achieves a practical compromise between measurement resolution and the number of resistors required. The sensor used in this example comprised 1280 resistors. A digital oscilloscope with a high bandwidth 500 probe was used to measure the voltage across x64 current shunt resistors 18.

Stimulator PCB

The stimulator PCB comprises a multi-electrode array formed from the conductive tracks of multiple electrodes and a set of connectors allowing current pulse to be fed into specific electrodes.

Figure 15:
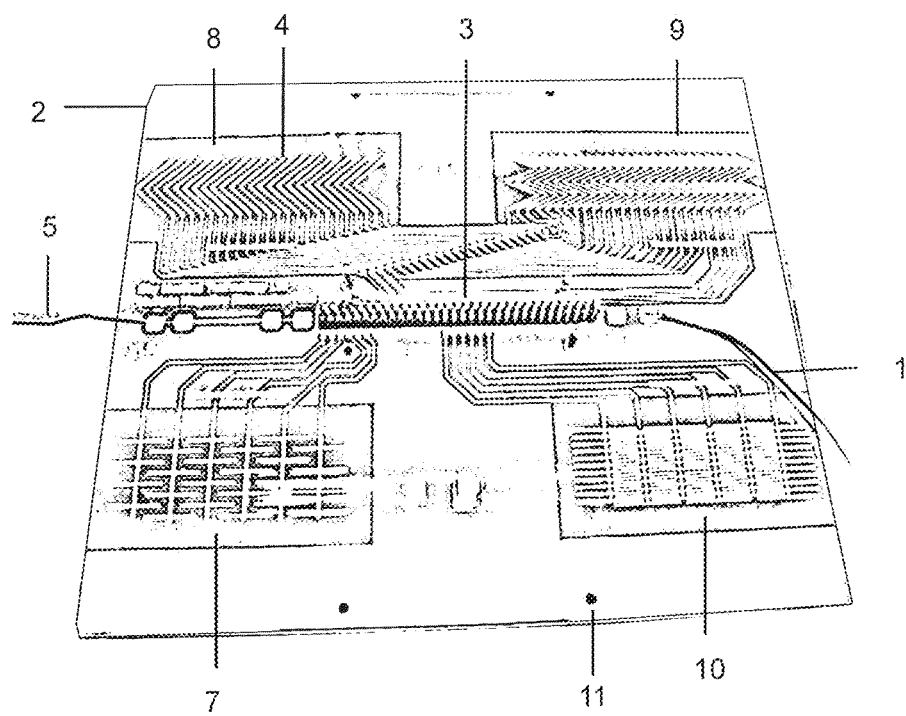
FIG. 15 is a photograph of a stimulator printed circuit board (PCB).

FIG. 15 shows an example stimulator PCB 2 possessing several styles and arrangements of electrodes 4, comprising interlocking zigzag electrode arrays 8 and 9, and interdigitating finger electrode arrays 7 and 10. In the present example, a standard "Firefly T-1" electrostimulation device (Firstkind Ltd) was used to feed current pulses of 27 mA into wire 5. The central pin header 3 connects the current pulses fed into the stimulator via wire 5 to individual electrodes 4 using jumper links. Wire 1 connects to the current return path and acts as a noise screen. Alignment holes 11 allow accurate positioning of the sensor 15 over the stimulator 2 using connector pins.

Within the stimulator 2, the electrodes of array 7 are 0.3 mm wide and positioned 10 mm apart. The width of the electrode footprint of these electrodes is 14 mm. The electrodes of array 9 are 0.3 mm wide and positioned 3 mm apart. The width of the electrode footprint of these electrodes is 10.3 mm.

Method of Stimulation

Figure 16:
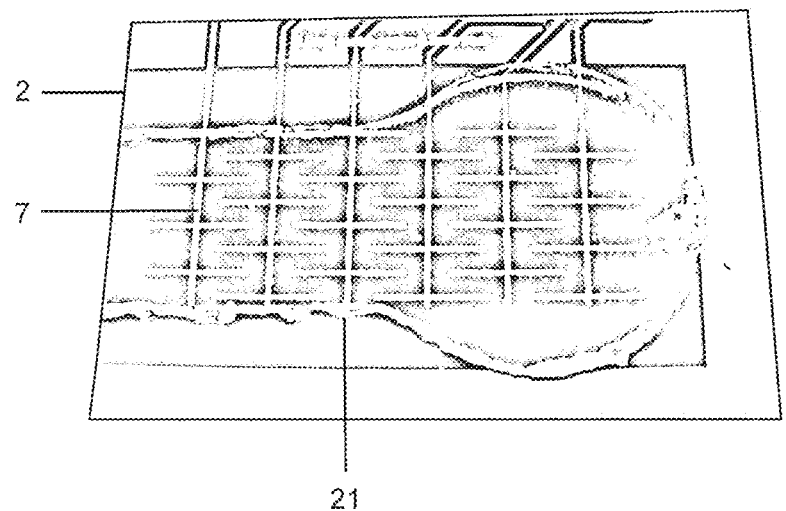
FIG. 16 shows the connection of a stimulator PCB to a sensor PCB.
Figure 16:
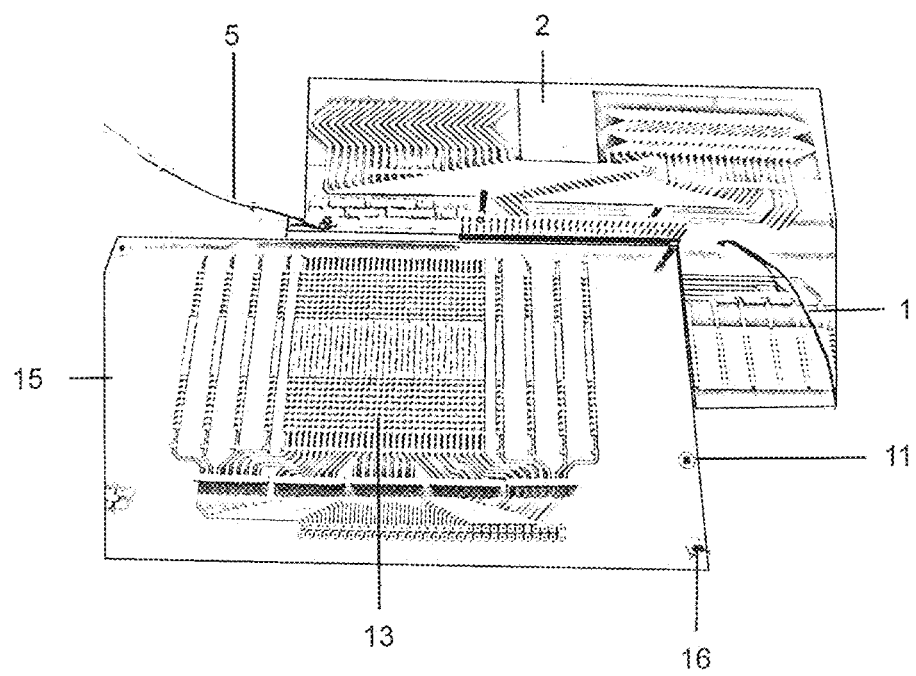

A 0.8 mm layer of hydrogel 21 was placed on an array (7 or 9) of the stimulator 2 (FIG. 16A). The array (7 or 9) was then accurately positioned below the highest resolution area 19 of the sensor 15 and the sensor 15 secured in place using connector pins 16 (FIG. 16B).

The stimulator 2 was then used to apply electrical stimulation to the sensor 15 via activation of individual or groups of electrodes 4 within the array (7 or 9). The peak voltage was measured on each of the current measuring resistors 17 of the sensor 15. The next electrode 4 or group of electrodes within the array (7 or 9) was activated and the peak voltage measurements in each of the resistors 17 repeated. These steps were repeated for all desired electrodes and adjacent electrode pairs within the array (7 or 9). The current in each column of pads 14 was calculated using the known probe attenuation and current shunt resistance. The current density in each column was then calculated using the known pad 13 dimensions.

Results

Zigzag Electrode Array

Figure 17:
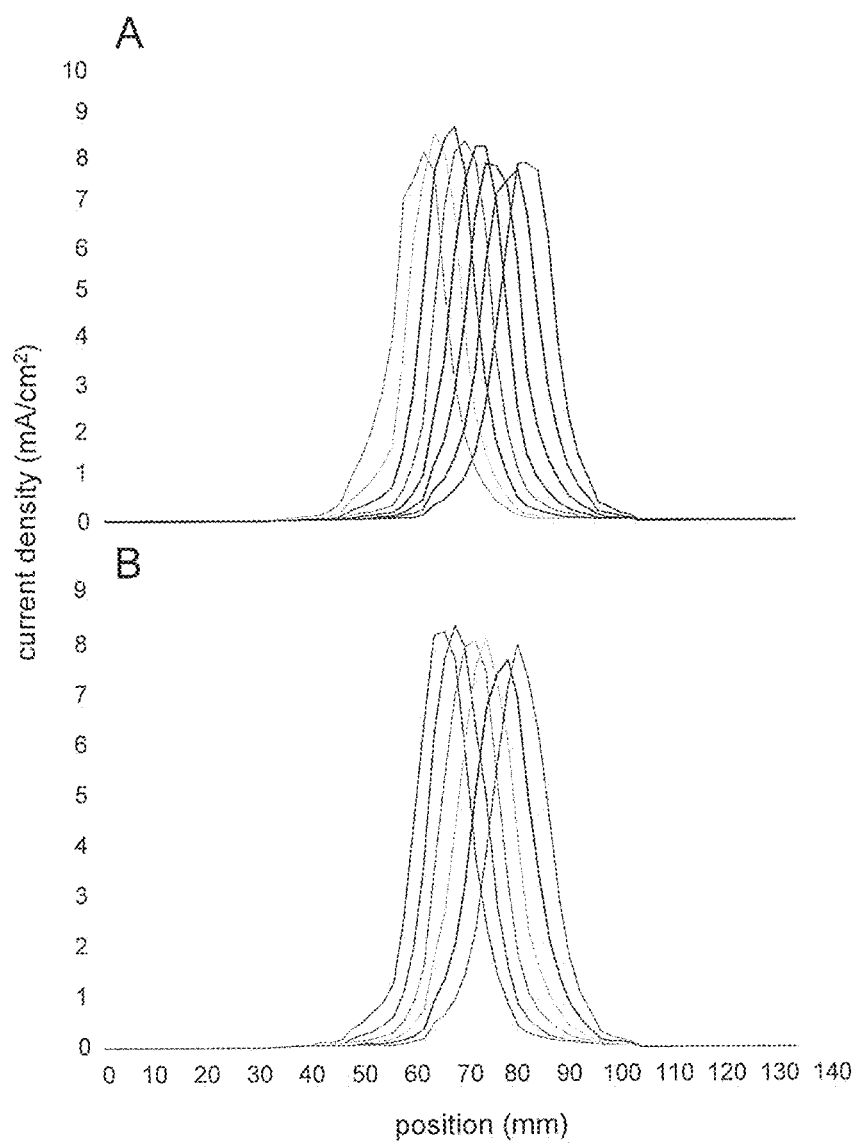
FIG. 17 shows the current density within a sensor PCB during stimulation by different electrodes within a zigzag electrode array.

The position of the current density within the sensor 15 was calculated during sequential activation of adjacent electrodes (FIG. 17A) or adjacent pairs of electrodes (FIG. 17B) within array 9. Each trace of FIG. 17 represents activation of a single electrode (A) or pair of electrodes (B) within array 9.

Activation of individual electrodes or adjacent pairs of electrodes within array 9 induced electrical fields within the sensor of width 11.9 mm and 12.3 mm respectively (Table 1). Activation of adjacent electrodes or pairs of adjacent electrodes within the array allowed movement of the effective electrode position by steps smaller than the width of the electrode footprint of the individual electrodes or electrode pairs along the same axis (2.8 mm vs 10.3 mm and 2.9 mm vs 13.3 mm respectively).

The zigzag configuration of the electrodes allowed the conductive track of each electrode in the array to be positioned so as to overlap with the electrode footprint of an adjacent electrode within the array. The results demonstrate that the effective electrode position can thereby be moved from one electrode to an adjacent electrode in the array by a distance smaller than the width of the electrode footprint of the electrodes along the same axis.

Interdigitating Electrode Array

Figure 18:
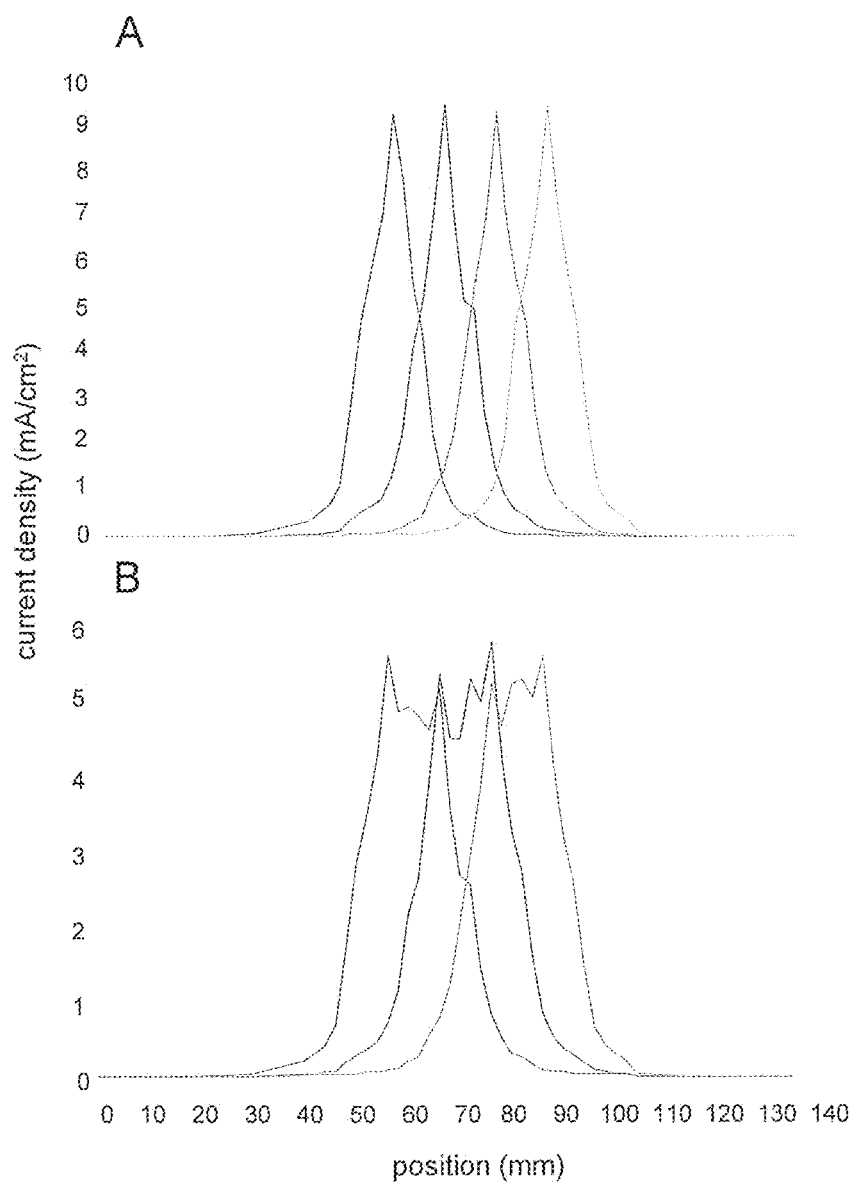
FIG. 18 shows the current density within a sensor PCB during stimulation by different electrodes within an array of interdigitating electrodes.

The position of the current density within the sensor 15 was calculated during sequential activation of adjacent electrodes (FIG. 18A) or adjacent pairs of electrodes (FIG. 18B) within the array 7. Each trace of FIG. 18 represents activation of a single electrode (A) or pair of electrodes (B) within the array 7.

Activation of individual electrodes or adjacent pairs of electrodes within the array 7 induced electrical fields within the sensor of width 11.9 mm and 19.9 mm respectively (Table 1). Activation of adjacent electrodes or pairs of adjacent electrodes within the array allowed movement of the effective electrode position by steps smaller than the width of the electrode footprint of the individual electrodes or pairs of adjacent electrodes along the same axis (10.5 mm vs 14.0 mm and 10.7 mm vs 24.0 mm respectively).

The interdigitating configuration of the electrodes within the array 7 allows the conductive track of each electrode in the array to be positioned so as to overlap with the electrode footprint of an adjacent electrode within the array. The results demonstrate that the effective electrode position can thereby be moved from one electrode to an adjacent electrode in the array by a distance smaller than the width of the electrode footprint of the electrodes along the same axis.

TABLE 1

| Electrode | Electrode Energisation | Width of electrode footprint (mm) | Width of electrical field (Width of half peak amplitude) (mm) | With of movement (mm) |
|---|---|---|---|---|
| Zigzag | Single | 10.3 | 11.9 | 2.8 |
|  | Adjacent pairs | 13.3 | 12.3 | 2.9 |
| Interdigitating | Single | 14.0 | 11.9 | 10.5 |
|  | Adjacent pairs | 24.0 | 19.9 | 10.7 |

The invention claimed is:

1. A device for neuromuscular stimulation, comprising:
a) a positive electrode,
b) at least three negative electrodes,
c) a non-conductive substrate, and
d) a control unit for activating the at least three negative electrodes,
wherein the control unit activates the at least three negative electrodes in a predetermined sequence, so as to deliver electrical stimulus to a user, wherein the predetermined sequence is repeated with an increasing level of stimulus until a predetermined outcome is achieved,
wherein each negative electrode is a conductive track mounted on the non-conductive substrate,
wherein a first negative electrode forms a first pattern, a second negative electrode forms a second pattern, and a third negative electrode forms a third pattern,
wherein the first pattern interdigitates or interleaves with the second pattern, and
wherein the second pattern interdigitates or interleaves with the third pattern.

2. The device of claim 1 wherein the conductive track of the first negative electrode overlaps with 0.5-1%, 1-10%, 10-25%, 25-50% or more than 50% of an electrode footprint of the second negative electrode.

3. The device of claim 1 wherein the first negative electrode comprises a central section of the conductive track from which issue a series of digits.

4. The device of claim 3 wherein the central section of the conductive track is linear.

5. The device of claim 3 wherein the series of digits are parallel to each other.

6. The device of claim 3 wherein the series of digits are linear.

7. The device claim 3 wherein the series of digits are perpendicular to the central section of the conductive track.

8. The device of claim 3 wherein the series of digits are curved.

9. The device of claim 3 wherein the second negative electrode possesses a same geometry as the first negative electrode.

10. The device of claim 1 wherein the conductive track of the first negative electrode is a zigzag of conductive track.

11. The device of claim 10 wherein the zigzag is "w" in shape.

12. The device of claim 10 wherein the zigzag is regular.

13. The device of claim 12 wherein the corners of the zigzag form a right angle.

14. The device of claim 10 wherein the second negative electrode is a zigzag nested within the first negative electrode.

15. The device of claim 14 wherein arrangement of the first negative electrode and the second negative electrode allows positional increments smaller than half of the size of an electrode footprint of the first negative electrode along a same axis.

16. The device of claim 15 wherein the arrangement of the first negative electrode and the second negative electrode allows positional increments smaller than a quarter of the size of the electrode footprint of the first negative electrode along the same axis.

17. The device of claim 1 wherein the at least three negative electrodes form a matrix of overlapping electrodes.

18. The device of claim 1 wherein the at least three negative electrodes are arranged radially.

19. The device of claim 18 wherein the at least three negative electrodes form one or more radial borders around a central radial pattern.

20. The device of claim 19 wherein the at least three negative electrodes that form the one or more radial borders interlock with negative electrodes that form the central radial pattern.

21. The device of claim 1 wherein the predetermined sequence includes sequential activation of combinations of two or more adjacent negative electrodes.

* * * * *